US00PP17939P2

(12) United States Plant Patent
Hanes

(10) Patent No.: US PP17,939 P2
(45) Date of Patent: Aug. 21, 2007

(54) *PETUNIA* PLANT NAMED 'WHIP BURGTO'

(50) Latin Name: ***Petunia* sp.**
Varietal Denomination: Whip Burgto

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,367

(22) Filed: Mar. 7, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by medium, deep burgundy-purple flowers, medium-green foliage with elliptical to ovate leaves, a small to medium, round, bushy, tight and compact plant habit with moderately vigorous growth, an initially spreading to decumbent to semi-trailing plant habit with an early and continuous flowering response, is disclosed.

1 Drawing Sheet

Genus and species: *Petunia* sp.
Variety denomination: 'Whip Burgto'.

BACKGROUND OF THE NEW PLANT

The present invention comprises a new and distinct cultivar of *petunia,* botanically known as a *Petunia* sp., and hereinafter referred to by the cultivar name 'Whip Burgto'. The new cultivar originated from a hybridization made in November 2002 in Gilroy, Calif. The female parent was '1299-1', a light bluish-purple flowered proprietary *petunia* plant (unpatented), while the male parent was '1346-2', a proprietary red-flowered *petunia* plant (unpatented).

The new cultivar was created in 2002 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif., Hillscheid, Germany and Andijk, The Netherlands. The present invention has been found to retain its distinctive characteristics through successive asexual propagations.

Plant Breeder's Rights for this cultivar were applied for in Canada on Jul. 19, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium-sized deep burgundy-purple flowers;
2. Medium-green foliage with elliptical to ovate leaves;
3. A small to medium-sized, round, bushy, compact, tight plant habit;
4. Moderately vigorous growth;
5. An initially spreading to decumbent to semi-trailing plant habit; and
6. An early and continuous flowering response.

DESCRIPTION OF PHOTOGRAPH

This new *petunia* plant is illustrated by the accompanying photograph which shows the overall plant habit including blooms, buds, and foliage of the plant; the colors shown are as true as can be reasonably obtained by conventional photographic procedures. The photograph is of a 3-month-old plant grown in a greenhouse in Hillscheid, Germany.

DESCRIPTION OF THE NEW CULTIVAR

The following detailed description sets forth the distinctive characteristics of 'Whip Burgto'. The data which define these characteristics were collected from asexual reproductions carried out in Hillscheid, Germany. The plant history was taken on 5 to 6-week old plants which were planted as rooted cuttings in 12-cm pots in early July 2005 and grown in a greenhouse. The plants were pinched once. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia* sp.
- *Common name.*—*Petunia.*

Parentage:
- *Female parent.*—'1299-1' a proprietary light bluish-purple flowered *petunia* plant (unpatented).
- *Male parent.*—'1346-2', a proprietary *petunia* plant having red flowers (unpatented).

Growth:
- *Form.*—Herbaceous annual.
- *Habit.*—Spreading initially, to a decumbent or trailing plant habit; pinching enhances the formation of branches.
- *Height* (*measured from the top of the soil*).—11.0 cm.

*Width* (*horizontal plant diameter*).—22.6 cm.
*Propagation.*—Terminal tips for cutting.
*Time to produce a finished flowering plant.*—About 10 weeks for a 12-cm pot in the Spring.
*Outdoor plant performance.*—Use in hanging baskets and containers.
*Time to initiate and develop roots.*—About 25 days.
*Root description.*—Fibrous, self-branching.

Stems:
*Average number* (*basal*).—4.3.
*Length of basal branches* (*from the base of the stem to the tip*).—17.3 cm.
*Internode length.*—3.1 cm.
*Diameter of branches* (*from midpoint*).—0.4 cm.
*Stem color.*—RHS 143C.
*Anthocyanin.*—Absent.
*Texture.*—Pubescent.

Leaves:
*Arrangement.*—Initially alternate, opposite at flowering branches.
*Size.*—Length: 5.3 cm. Width: 3.4 cm.
*Shape.*—Ovate to elliptical.
*Margin.*—Entire.
*Apex.*—Obtuse to acute.
*Base.*—Attenuate.
*Color.*—Upper surface: RHS 138A (medium-green). Lower surface: Between RHS 134B and RHS 144A (yellowish-green).
*Texture.*—Smooth, nearly glabrous with relatively sparse pubescence.
*Venation.*—Mainly pinnate.
*Venation color.*—Upper surface: Hardly visible. Lower surface: RHS 144B.
*Petioles.*—General: Not clearly distinct from the leaf blade. Length: 0.2 cm to 0.5 cm. Width: 0.2 cm to 0.4 cm. Color: RHS 144C. Texture: Pubescent along the edge.

Flower bud:
*Shape.*—Tube-shaped, furrowed.
*Size.*—Length: 3.1 cm. Diameter: Up to 0.8 cm.
*Color at tight bud.*—RHS N77D at the base and RHS N77B (dull-purple) near the tips.
*Immature flower color.*—RHS N186D (deep bluish-purple).

Inflorescence:
*Blooming habit.*—Flowers appear about 8–9 weeks after planting of rooted cuttings; continuous from Spring through Fall, still flowering at relatively low light conditions in late autumn, appear floriferous.
*Inflorescence type.*—Flowers appear solitary on pedicels, emerging singularly at the nodes.
*Floret type.*—5 petals, mainly fused, funnel-shaped, the free lobes are directed outward.
*Number of flowers per node.*—1.
*Lastingness of individual blooms on the plant.*—6 to 8 days.
*Fragrance.*—Weak, *petunia*-like.
*Pedicels.*—Color: RHS 143C. Length: 4.3 cm. Diameter: 0.1 cm to 0.15 cm. Texture: Covered with short pubescence.

Flowers:
*Shape.*—Funnel-shaped, formed by 5 fused petals.
*Size.*—Diameter (flower face): 4.7 cm. Depth (total length of flower): 3.3 cm. Funnel: Length: 2.6 cm. Diameter (at opening): About 1.1 cm. Outside texture: Pubescent; rough with coarse hair, mostly along the veins.
*Mature flower.*—Face/Margin Color: Upper surface: RHS 61A or deeper than RHS N66A, with RHS N79B weak, fine and dark veins. Lower surface: RHS 71C.
*Corolla.*—Shape of corolla: Tube-shaped. Color inside (throat): RHS 79A (blackish-purple). Color outside: RHS N77B.
*Petals.*—Apex: Weakly rounded, nearly truncate. Base: Fused. Margin: Entire. Waviness: Moderately wavy. Lobation: Weak. Texture: Smooth.
*Calyx.*—Composed of 5 sepals fused at the base.
*Sepals.*—Number: 5. Color: Upper surface: RHS 143A. Lower surface: RHS 143C. Length: 1.8 cm. Width: Up to 0.5 cm. Shape: Lanceolate or narrowly elliptic. Apex: Obtuse. Base: Fused. Margin: Entire. Texture: Pubescent (relatively thin).

Reproductive organs:
*Stamens.*—Number: 5. Filament color: RHS 155D (white). Filament length: 1.4 cm to 1.7 cm. Filament diameter: 0.1 cm. Pollen color: RHS 4D (pale-yellow). Pollen amount: Moderate.
*Pistil.*—Number: 1. Length: 1.8 cm. Diameter: 0.1 cm. Stigma color: RHS 145A (light-green). Style color: RHS 145D (pale light-green). Style length: About 1.5 cm.

Fruit and seed set: No seed set observed so far.
Disease and insect resistance: No particular resistance or susceptibility has been observed.

COMPARISON WITH PARENTAL AND COMMERCIAL CULTIVARS

'Whip Burgto' differs from the female parent '1299-1' (unpatented) by having burgundy-purple flowers, while '1299-1' has light-purple flowers. In addition, 'Whip Burgto' has a more vigorous growth habit and has and earlier flowering response than '1299-1'.

'Whip Burgto' differs from the male parent '1346-2' (unpatented) by having burgundy-purple flowers, while '1346-2' has red flowers. In addition, 'Whip Burgto' has a more compact plant habit with shorter internodes than '1346-2'.

'Whip Burgto' differs from the commercial variety 'Whip Pur' (U.S. Plant Pat. No. 15,480) by having larger, deeper and less bluish flowers than 'Whip Pur'. In addition, 'Whip Burgto' has lighter green foliage than 'Whip Pur'.

'Whip Burgto' differs from the commercial variety 'Whip Burg' (U.S. Plant Pat. No. 14,258) by having smaller, more cherry-red flowers with less bluish undertones than 'Whip Burg'. In addition, 'Whip Burgto' has an earlier flowering response and a more compact plant habit than 'Whip Burg'.

I claim:

1. A new and distinct cultivar of *petunia* plant as shown and described herein.

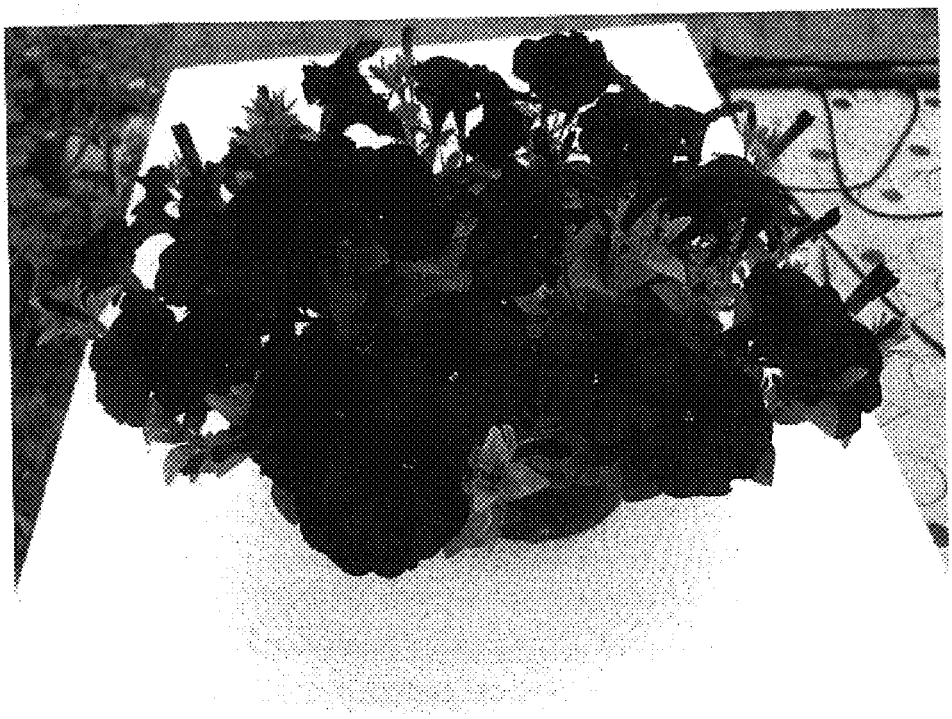

* * * * *